(12) United States Patent
Nagamine et al.

(10) Patent No.: US 7,192,617 B2
(45) Date of Patent: Mar. 20, 2007

(54) WHITENING AGENT, SKIN PREPARATION FOR EXTERNAL USE AND COSMETIC

(75) Inventors: Kenichi Nagamine, Tokyo (JP); Miki Hayashi, Tokyo (JP); Kaori Yamasaki, Nagasaki (JP)

(73) Assignee: Nichirei Biosciences Inc., Tokyo (JP)

( * ) Notice: Subject to any disclaimer, the term of this patent is extended or adjusted under 35 U.S.C. 154(b) by 0 days.

(21) Appl. No.: 10/537,958

(22) PCT Filed: Dec. 8, 2003

(86) PCT No.: PCT/JP03/15656

§ 371 (c)(1),
(2), (4) Date: Jul. 22, 2005

(87) PCT Pub. No.: WO2004/054520

PCT Pub. Date: Jul. 1, 2004

(65) Prior Publication Data

US 2006/0104926 A1    May 18, 2006

(30) Foreign Application Priority Data

Dec. 13, 2002 (JP) .............................. 2002-362507

(51) Int. Cl.
*A61K 36/00* (2006.01)
(52) U.S. Cl. ...................... 424/776; 424/725
(58) Field of Classification Search ............. None
See application file for complete search history.

(56) References Cited

FOREIGN PATENT DOCUMENTS

| | | | |
|---|---|---|---|
| EP | 0 435 556 A1 | | 7/1991 |
| JP | 09-221429 A1 | | 8/1997 |
| JP | 11-246336 A1 | | 9/1999 |
| JP | 11246336 A | * | 9/1999 |
| JP | 2000-327549 A1 | | 11/2000 |
| JP | 2000-327550 A1 | | 11/2000 |
| JP | 2000319154 A | * | 11/2000 |
| JP | 2000327549 A | * | 11/2000 |
| JP | 2000327550 A | * | 11/2000 |
| JP | 2000327553 A | * | 11/2000 |
| JP | 2001-031558 A1 | | 2/2001 |
| JP | 2001031558 A | * | 2/2001 |

OTHER PUBLICATIONS

Phytochemicals.info/phytochemicals/gallic-acid.php.*

* cited by examiner

*Primary Examiner*—Christopher R. Tate
*Assistant Examiner*—Melenie McCormick
(74) *Attorney, Agent, or Firm*—Darby & Darby

(57) ABSTRACT

The invention relates to a whitening agent that makes effective use of camu camu seeds, which have conventionally been discarded, and that has high safety and whitening effect useful in cosmetics and the like, as well as skin preparations for external use and cosmetics containing the whitening agent. The whitening agent of the present invention contains camu camu seed extract as an active component, and the skin preparations for external use and cosmetics of the present invention contain the whitening agent.

8 Claims, 8 Drawing Sheets

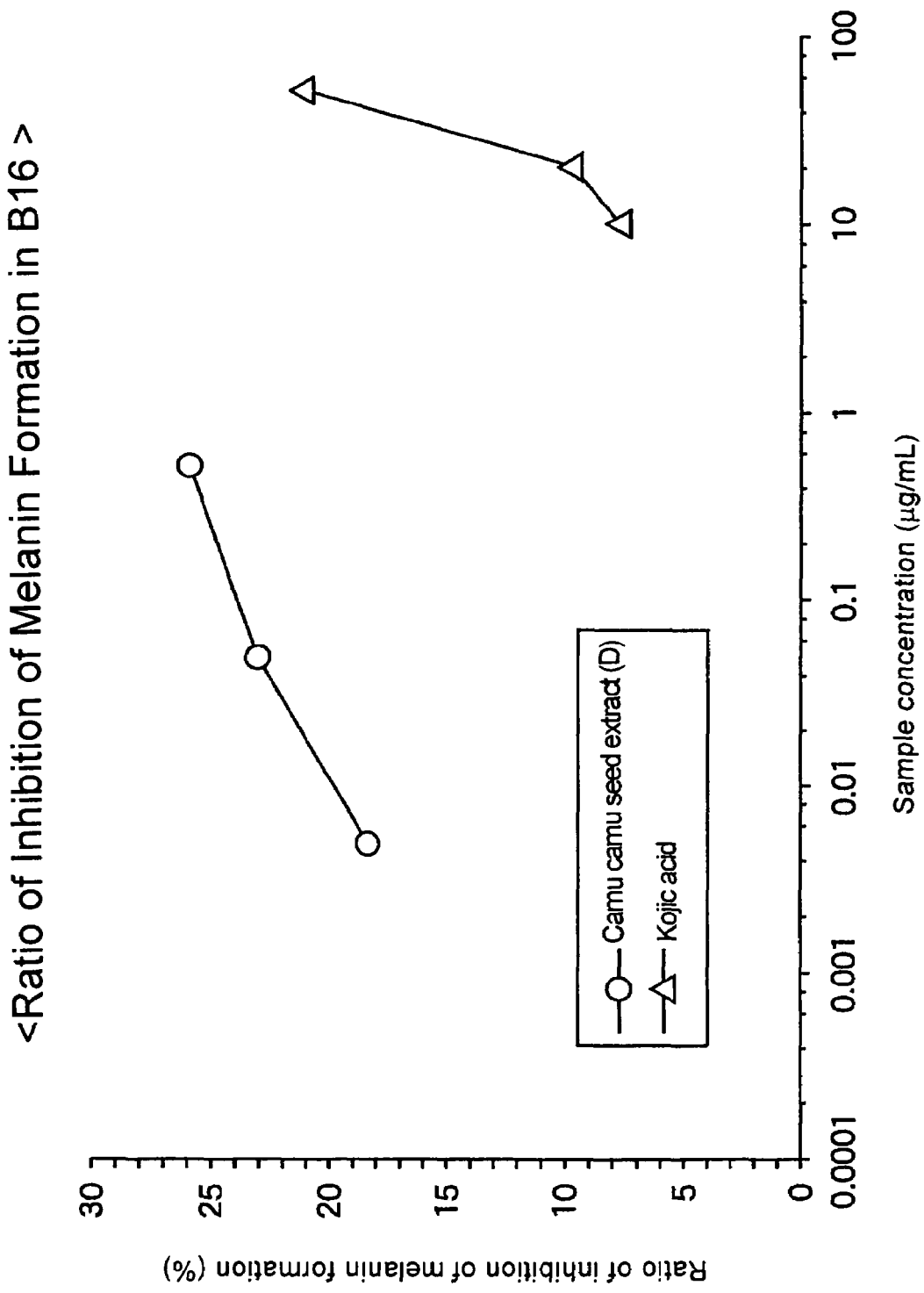

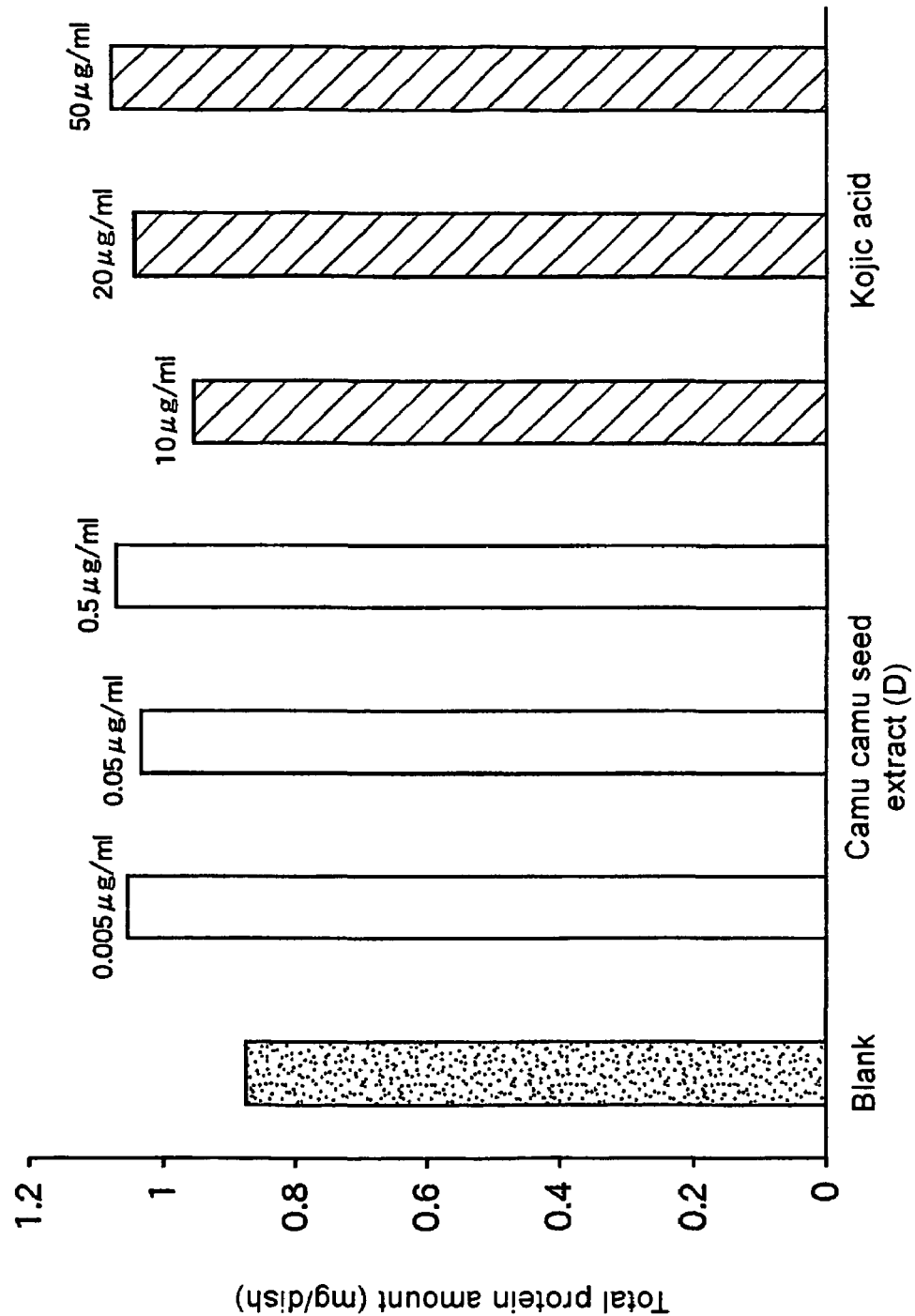

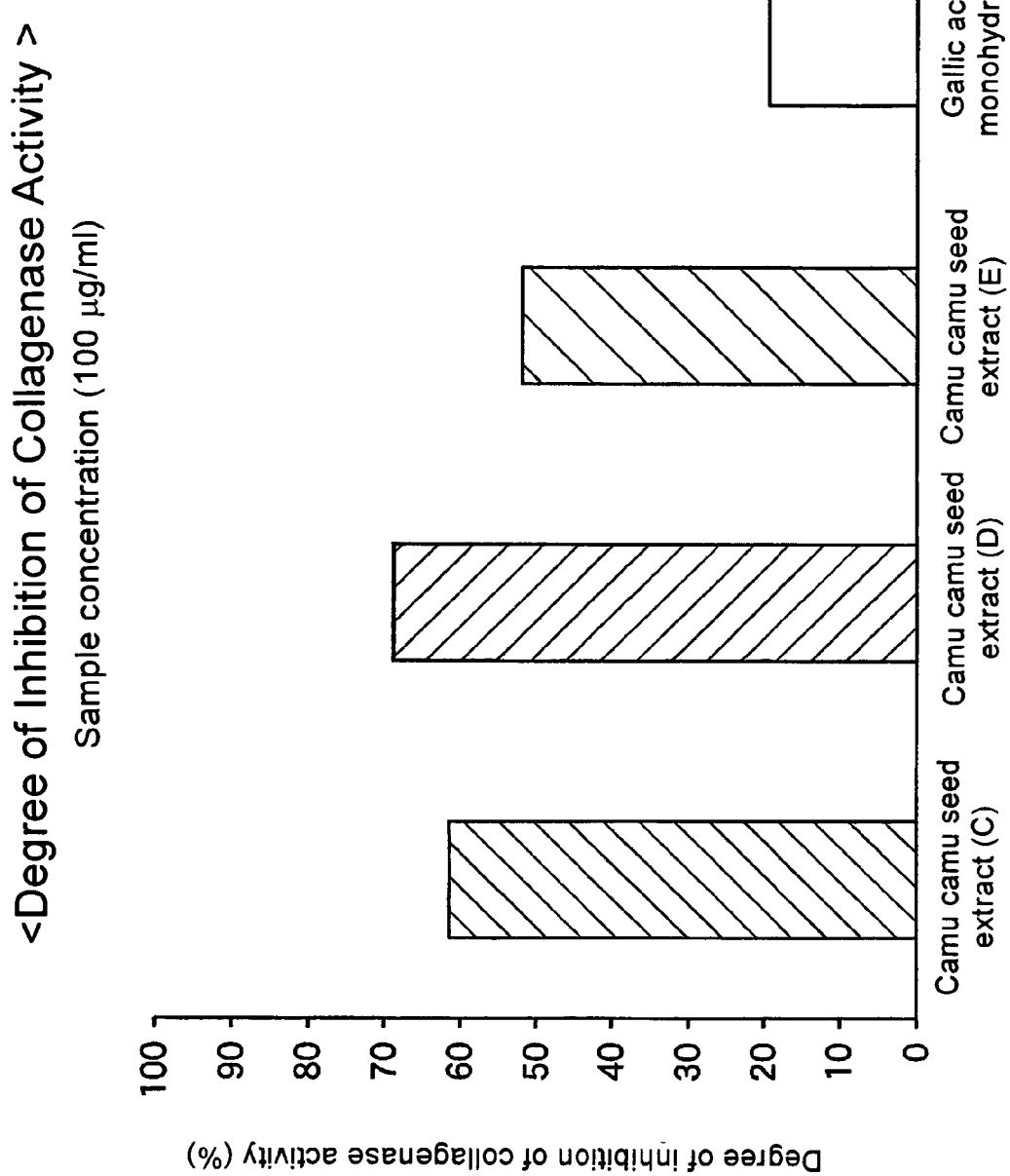

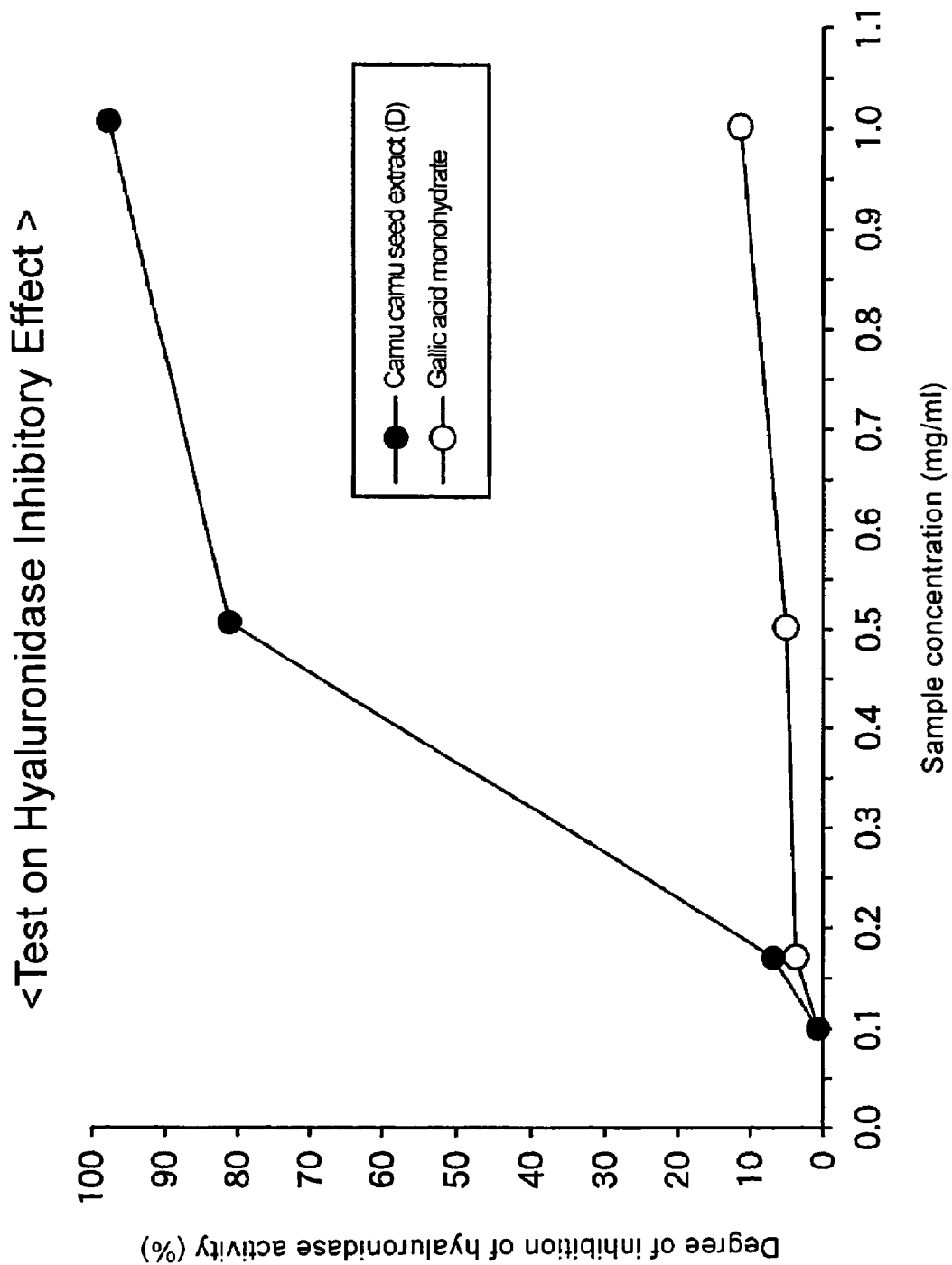

WHITENING AGENT, SKIN PREPARATION FOR EXTERNAL USE AND COSMETIC

FIELD OF ART

The present invention relates to whitening agents containing camu camu seed extract as an active component, and to skin preparations for external use and cosmetics using the same.

BACKGROUND ART

In recent cosmetics and food industries, there are growing fears about health hazards of materials of animal origin, and regulations for such materials are being tightened, which gives rise to stronger interest in materials of plant origin. On the other hand, serious problems are arising, such as acceleration of ageing by oxidation of active oxygen taken into or generated within the body, and skin coloration by UV rays or carcinogenicity thereof.

For example, food, cosmetics, and the like articles are suffering from oxidation or peroxidation of oils and fats contained in various materials thereof, caused by atmospheric oxygen during manufacture, processing, storage, or preservation of such articles. Unsaturated fatty acids contained in oils and fats, such as linoleic and linolenic acids, are known to be particularly prone to peroxidation by atmospheric oxygen to generate lipid peroxides, free radicals, or even carcinogenic substances. Oxidation and peroxidation cause change of the products in appearance, such as coloration, discoloration, denaturalizaton, or abnormal odor, or in quality, such as decrease in effective nutritional value. Further, denaturalization may cause generation of toxic substances, which results in deterioration of product quality.

In order to inhibit such oxidation and peroxidation of unsaturated fatty acids, and to prevent deterioration of product quality, various antioxidants have conventionally been used. Antioxidants act on peroxide radicals, which are generated in oxidation, to terminate chain oxidation, or alternatively act on free radicals to terminate oxidative reaction. Commonly used antioxidants are synthetic antioxidants, such as butylhydroxyanisol (BHA) and butylhydroxytoluene (BHT). Recently, however, effects and safety of synthetic antioxidants on the human body have come to be questioned as their use expands, and consumers are presenting growing rejections. Further, synthetic antioxidants are oil soluble, and thus are hard to use in aqueous solutions.

On the other hand, as natural antioxidants of high safety, natural vitamin E ($\alpha$-tocopherol), vitamin C, and the like are known. However, the properties of these natural antioxidants are in either extreme, i.e., either extremely fat- or water-soluble, so that their applications are naturally limited. The natural antioxidants also have disadvantages in that their activity cannot be maintained stably for a prolonged period of time.

There is thus a strong demand for natural antioxidants having strong antioxidative activity, high water-solubility, and long-termstability in antioxidative activity.

Pigmentation, such as skin coloration or age spots, is caused by intrinsic factors such as metabolic defects in living organism, and extrinsic factors such as UV rays. Pigmentation caused by the latter extrinsic factors is more common, wherein UV rays stimulate melanocytes to activate the same, which in turn activates tyrosinase to induce skin pigmentation. It is known that inhibition of the melanocyte activity to thereby inhibit generation of tyrosinase and melanin pigment results in prevention of pigmentation such as skin coloration or age spots. In the cosmetic industry, much importance has been placed on development of substances having whitening effects, and various whitening agents have been developed. In addition, UV dose is recently increasing due to ozone depletion or other factors. This further stimulates consumer's demand for measures against UV, and safe and effective whitening agents.

Collagen and hyaluronic acid are known to have effects on moisture retaining property, softness, and elasticity of skin. Collagen constitutes 90% of dermis of skin and is distributed all over the dermis to give appropriate elasticity and strength to the skin. Hyaluronic acid is widely distributed over living organisms such as skin, synovial fluid, corpus vitreum, ligament, and the like, and contributes in skin to cell adhesion, cell protection, formation of skin tissues, retainment of tissue moisture, and maintenance of softness. Collagen and hyaluronic acid are known to be decomposed in vivo with enzymes called collagenase and hyaluronidase, respectively. It is said that, when these enzymes decompose collagen and hyaluronic acid to decrease their amounts, skin loses moisture and tension, and develops wrinkles and sagging, which are typical symptoms of skin ageing.

In expectation of anti-ageing and anti-wrinkle effects on skin, it is proposed to add substances that inhibit activities of these enzymes, to skin preparations for external use and various cosmetics, and various collagenase inhibitors and hyaluronidase inhibitors have been developed to date.

Camu camu fruit, which is recognized as a vitamin C-rich plant like acerola fruit, is commercially sold in South America as cosmetics or food, and is recently imported and sold also in Japan as a food material. Since the major component of camu camu fruit is vitamin C, its extract finds applications in antioxidants, moisture retainers, and whitening agents (for example, JP-9-221429-A, JP-11-246336-A, JP-2000-327549-A, JP-2000-327550-A, and JP-2001-31558-A).

However, only the pulp of camu camu fruit, which has a high vitamin C content, is used in cosmetics and food, and the seeds, which has only a slight vitamin C content, hardly find effective use and are discarded.

SUMMARY OF THE INVENTION

It is therefore an object of the present invention to provide a whitening agent that makes effective use of camu camu seeds, which have conventionally been discarded, and that has high safety and whitening effect useful in skin preparations for external use and cosmetics, as well as a skin preparation for external use and cosmetics containing the whitening agent.

It is another object of the present invention to provide a skin preparation for external use and cosmetics that are expected to have stable antioxidative effect, collagenase inhibitory effect, and hyaluronidase inhibitory effect, excellently safe, and expected to have anti-ageing and anti-wrinkle effects on skin.

In order to achieve the above objects, the present inventors have first made intensive studies for usefulness of camu camu seeds, which have been discarded after the fruit is squeezed for juice. Through the studies, the inventors have found out that extract of camu camu seeds has strong antioxidative effect, whitening effect, collagenase inhibitory effect, hyaluronidase inhibitory effect, and even anti-ageing effect that may be utilized in skin preparations for external use, cosmetics, and the like, to thereby complete the present invention.

According to the present invention, there is provided a whitening agent comprising camu camu seed extract as an active component.

According to the present invention, there is also provided a skin preparation for external use or a cosmetic comprising the above whitening agent.

BRIEF DESCRIPTION OF THE DRAWINGS

FIG. 5 is a graph showing the results of the test on inhibition of melanin formation conducted in Example 1.

FIG. 6 is a graph showing the results of the measurement of the total protein amount of each culture medium conducted in Example 1.

FIG. 7 is a graph showing the results of the test on collagenase inhibitory effect conducted in Referential Example 6.

FIG. 8 is a graph showing the results of the test on hyaluronidase inhibitory effect conducted in Referential Example 7.

PREFERRED EMBODIMENTS OF THE INVENTION

Figure 1:
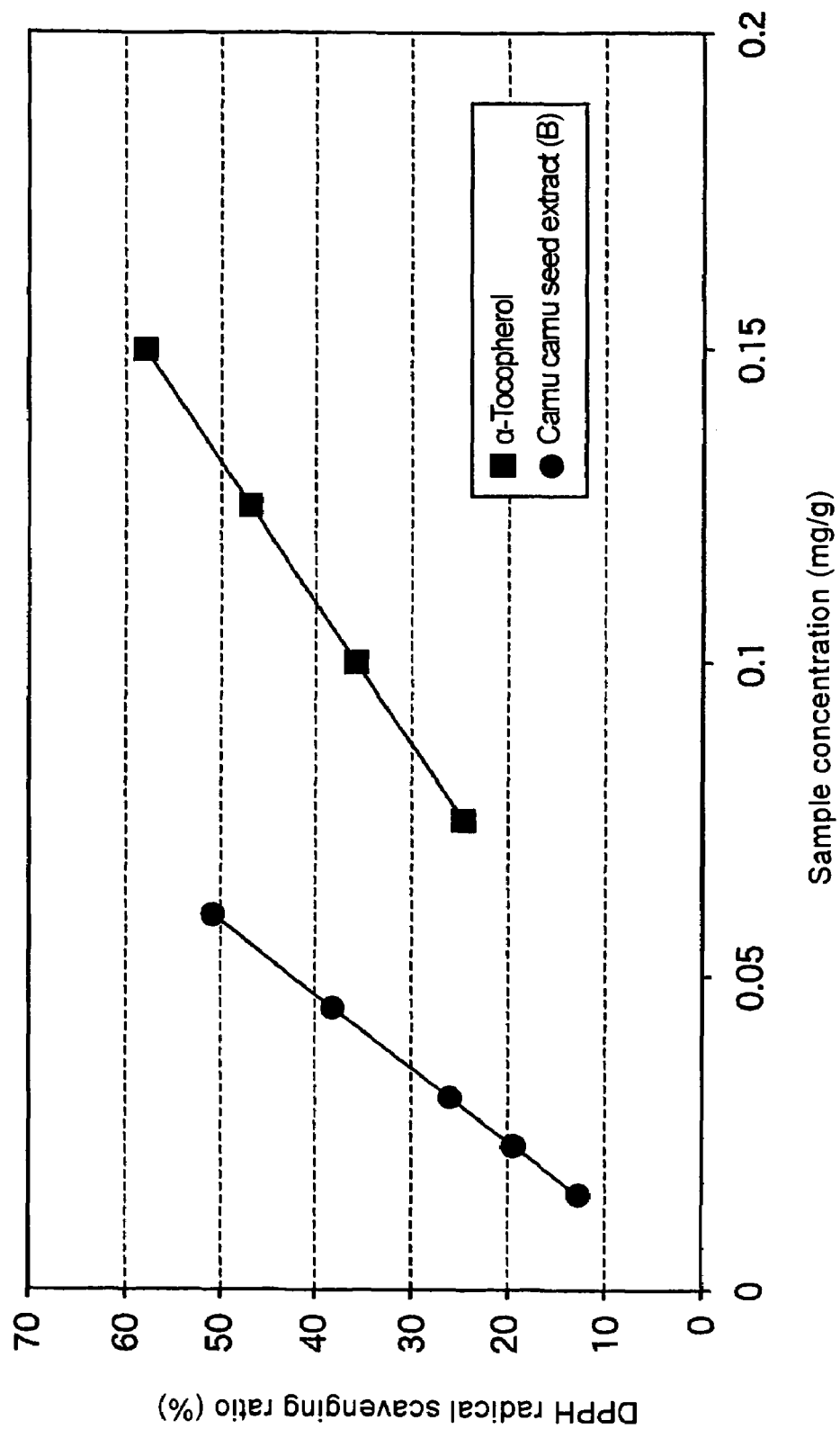
FIG. 1 is a graph showing the results of the test for measuring DPPH radical scavenging activity conducted in Referential Example 1.

The present invention will now be explained in detail.

The whitening agent according to the present invention contains camu camu seed extract as an active component. This extract is also useful as an active component of an antioxidant, a collagenase inhibitor, a hyaluronidase inhibitor, and an anti-ageing agent. The camu camu seeds used as a material of the extract are seeds of camu camu (*Myrciaria dubia*), which is a fruit tree of the genus *Myrciaria*, of the family Myrtaceae.

Camu camu grows in the fluvial wetlands in the tropical rain forest in Central and South America, and is a bush of 2 to 3 m tall with red fruits of 2 to 3 cm in diameter. The cam camu fruit is known to be rich in vitamin C, but the camu camu seeds are substantially free of vitamin C, so that the seeds are rarely used and are therefore discarded.

An experiment shows that camu camu fruit extract usually has a vitamin C content of 1789 mg/100 g (1485 mg/100 g of ascorbic acid+295 mg/100 g of dehydroascorbic acid), but camu camu seed extract usually has a vitamin C content of only 1 mg/100 g (0 mg/100 g of ascorbic acid+1 mg/100 g of dehydroascorbic acid).

The camu camu seed extract contained as an active component in the whitening agent, antioxidant, collagenase inhibitor, hyaluronidase inhibitor, and anti-ageing agent of the present invention, is not particularly limited as long as it is extracted from camu camu seeds with an extractant. The extract may be in the form of an extract liquid, or an extract solid obtained by concentrating or drying the extract liquid.

The extraction may be made by a single extraction operation, or a plurality of extraction operations with various extractants as desired.

It is preferred that the camu camu seed extract is extracted so that it contains gallic acid or a salt thereof.

The extractant may be, for example, water, organic solvents, or the like, and the organic solvent may either be hydrophilic or hydrophobic. The hydrophilic organic solvent may be a conventional organic solvent, for example, alcohols, such as methyl alcohol, ethyl alcohol, glycerin, propylene glycol, and 1,3-butylene glycol, acetone, tetrahydrofuran, acetonitrile, 1,4-dioxane, pyridine, dimethylsulfoxide, N,N-dimethylformamide, or acetic acid. The hydrophobic organic solvent may be a conventional organic solvent, such as hexane, cyclohexane, carbon tetrachloride, chloroform, dichloromethane, 1,2-dichloroethane, diethyl ether, ethyl acetate, benzene, or toluene. One or a combination of two or more of these organic solvents may be used. Among these, water and/or a hydrophilic organic solvent, specifically, methanol, ethanol, 1,3-butylene glycol, water, or mixtures or combinations of these are particularly preferred.

The conditions for extraction are not particularly limited. For example, the temperature may be 5 to 95° C., preferably 10 to 90° C., more preferably 15 to 85° C., and even the room temperature will give good extraction. The extraction efficiency tends to be higher at higher temperatures. The extraction time may be a few hours to a few days, and the amount of extractant is usually 1 to 50 times, preferably 5 to 25 times the amount of the raw material by weight.

The extraction operation is not particularly limited, and may be performed according to a common procedure. For improving the extraction efficiency, the extraction may be performed under shaking, or in an extraction device equipped with a stirrer or the like. For example, camu camu seeds and an extractant may be stirred and shaken together, with or without preliminary soaking of the seeds in the extractant, and the resulting process liquid may be subjected to filtration, centrifugation, or decantation to separate the liquid into the extract liquid and the extract residue. The extract residue may further be subjected to a similar extraction process. The obtained extract liquid may be used as it is, or may further be concentrated and/or fractionated and purified, as desired.

The concentration process is not particularly limited, and may be performed by, for example, solvent removal, recovery of soluble components by making use of their solubility in water and/or an organic solvent, recovery of insoluble components, liquid-liquid separation with a water-hydrophobic organic solvent, recrystallization, reprecipitation, recovery of precipitate formed by cooling, or a combination of two or more of these.

The fractionation and purification process is not particularly limited, and may be performed by, for example, normal and/or reverse phase chromatography.

The camu camu seed extract preferably contains gallic acid and/or a salt thereof for use as an active component of the present whitening agent or antioxidant, and may contain gallic acid and/or a salt thereof for use as an active component of the present collagenase inhibitor, hyaluronidase inhibitor, or anti-ageing agent.

In the whitening agent, as well as the antioxidant, collagenase inhibitor, hyaluronidase inhibitor, or anti-ageing agent of the present invention, the content of the camu camu seed extract as an active component may suitably be selected depending on the form of use.

The skin preparation for external use and the cosmetics according to the present invention contain the present whitening agent. Further, skin preparations for external use and cosmetics containing at least one of the above whitening agent, antioxidant, collagenase inhibitor, hyaluronidase inhibitor, and anti-ageing agent may also be provided according to the invention.

The type of the cosmetics is not particularly limited, and may be, for example, skin care cosmetics such as skin lotion, emulsion, cream, face pack, and cleansing agents; make-up cosmetics such as lipsticks and foundation; or hair cosmetics. The cosmetics may be in any form without limitation. The skin preparation for external use may be, for example, ointment or various dermatological agents.

In the present skin preparation for external use and the cosmetics, the content of the present whitening agent, antioxidant, collagenase inhibitor, hyaluronidase inhibitor, or anti-ageing agent may suitably be selected depending on their kind, the kind and amount of other components to be mixed, and the form of the agent. Usually, the content is 0.001 to 20 wt %, preferably 0.01 to 10 wt % of the total amount of the skin preparation for external use or the cosmetics, in terms of dried camu camu seed extract.

The skin preparation for external use or the cosmetics according to the present invention may optionally contain various other components usually used as raw materials for cosmetics, as long as the desired effects of the present invention are not impaired. Examples of such other components may include water, oil solutions, surfactants, lubricants, alcohols, water-soluble polymeric agents, gelatinizers, moisture retainers, buffers, preservatives, antiinflammatory agents, thickeners, flavoring agents, vitamins, and whitening agents, antioxidants, collagenase inhibitors, hyaluronidase inhibitors, or anti-ageing agent other than those of the present invention. These may suitably be selected and combined for use, depending on the kind or purpose of the skin preparation for external use or cosmetics, and also on the form thereof.

Food having antioxidative effect may be provided by adding the antioxidant containing the camu camu seed extract as an active component. The food of the present invention may be of any type as long as the present antioxidant is contained, for example, candies, beverages, jam, or chewing gum. The food may be in any form without limitation.

In the food of the present invention, the content of the present antioxidant may suitably be selected depending on the kind of the food, the kind and amount of other components contained in the food. Usually, the content is 0.001 to 10 wt %, preferably 0.01 to 8 wt % of the total amount of the food, in terms of dried camu camu seed extract.

The food according to the present invention may optionally contain various other components usually used as raw materials for food, as long as the desired effects of the present invention are not impaired. Examples of such other components may include water, alcohols, sweeteners, acidulants, colorants, preservatives, flavoring agents, and excipients. These may suitably be selected and mixed depending on the kind and other purpose. of the food, or on the form thereof.

The whitening agent, and also the antioxidant, collagenase inhibitor, hyaluronidase inhibitor, and anti-ageing agent according to the present invention contain-camu camu seed extract as an active component, and accordingly have strong antioxidative effect, inhibitory effect on melanin formation, collagenase inhibitory effect, hyaluronidase inhibitory effect, and anti-ageing effect, as well as excellent safety.

Thus these agents of the present invention may be applied to skin preparations for external use or cosmetics, expecting the whitening effect and anti-ageing effect, or may also be applied to food, expecting the quality improvement and preventive effects against oxidation of food caused by active oxygen. Further, effective use of camu camu seeds, which have been an industrial waste, may be made.

EXAMPLES

The present invention will now be explained in more detail with reference to Referential Examples, Examples, and Prescription Examples, which are illustrative only and do not intend to limit the present invention.

Referential Example 1

Camu camu seeds were crushed, mixed with methanol, and stirred at 25° C. overnight for extraction. The mixture was centrifuged at 5° C. at 4000 rpm for 45 minutes, coasely filtered, and then passed through a 0.22 μm filter. The obtained methanol extract of camu camu seeds was vacuum distilled and evaporated to dry, and the resulting dry product was dissolved in purified water. To this solution, n-hexane was added, shaken for 5 minutes, and then left still, which operation was repeated until the n-hexane fraction was not colored, to thereby separate the water-soluble fraction from the n-hexane fraction. To the obtained water-soluble fraction, ethyl acetate was added, and fractionated in the same way as with n-hexane, to thereby separate the ethyl acetate fraction from the water-soluble fraction. The obtained ethyl acetate fraction was concentrated by vacuum distillation, and fractionated on a column of silica gel. The fractions were eluted in sequence with chloroform/methanol mixtures of eleven different ratios (10:0 to 0:10). The fractions eluted with 5:5 to 0:10 chloroform/methanol mixtures were collected, vacuum distilled, and evaporated to dry. The obtained dry product was dissolved in purified water.

This aqueous solution was purified on a C18 column, by putting the aqueous solution onto the C18 column, washing the column with purified water to collect the non-adsorbed fractions, and evaporating the collected fractions to dry. Here, the first non-adsorbed fraction obtained was a colored fraction, and the following non-adsorbed fraction was a transparent fraction, and thus two types of fractions were obtained. Each of the fractions was vacuum distilled and evaporated to dry to give sample (A), which was readily water-soluble, and sample (B), which was hardly water-soluble.

LCMS analysis was performed using an LCT mass spectrograph (manufacturedbyMICROMASS) withelectrospray ionization (ESI). NMR analysis was performed using UNITY plus 500 (manufactured by Varian) at $^1$H: 500.2 MHz and $^{13}$C: 125.8 MHz, with a solvent $D_2O$ for Sample (A) and $CD_3OD$ for Sample (B).

As a result of LCMS analysis of Sample (A), ions which appear to be deprotonated molecules ($(M-H)^-$) were observed at m/z169, and thus the molecular weight of the sample was believed to be 170. As a result of the NMR analysis, a single peak was observed at 7.062 ppm and a plurality of peaks were observed in 3.5–3.9 ppm in the $^1$H-NMR spectrum, while four peaks attributed to double-bonded carbons were observed in 110–146 ppm, and a peak attributed to a carbonyl carbon was observed at 175.8 ppm in the $^{13}$C-NMR spectrum. These spectral data were compared with those of a gallic acid sample, to find that the two matched in molecular weight, but were different in chemical shift of the carbon to which COOH is bonded. Thus this substance was identified as a gallate.

On the other hand, as a result of LCMS analysis of Sample (B), ions which appear to be deprotonated molecules ((M—H)$^-$) were observed at m/z169, and thus the molecular weight of the sample was believed to be 170. As a result of the NMR analysis, a single peak was observed at 7.060 ppm in the $^1$H-NMR spectrum, while five peaks were observed in the $^{13}$C-NMR spectrum. These spectral data were compared with those of a gallic acid sample, to find that the two matched in both chemical shift and molecular weight. Thus this substance was identified as a gallic acid.

The antioxidative activity of obtained extract (B) was determined in accordance with the following process.

<Test for Measuring DPPH Radical Scavenging Activity>

400 μl of extract (B), 1200 μl of 99.5% ethanol, and 1600 μl of a 0.25 M acetate buffer (pH 5.5) were placed in a test tube, and pre-incubated at 30° C. for 5 minutes. 800 μl of a 500 μM DPPH solution was added to the test tube, stirred, and reacted at 30° C. Exactly after 30 minutes of reaction, the absorbance of the sample at 517 nm was measured, using distilled water as a standard. From the measured absorbances, the DPPH radical scavenging ratio was calculated, and the 50% radical scavenging activity ($IC_{50}$) was obtained. The same procedure was performed with α-tocopherol, which is a known antioxidative component, for measuring the DPPH radical scavenging activity. The results are shown in FIG. 1.

From FIG. 1, it is understood that the 50% DPPH radical scavenging activity (abbreviated as $IC_{50}$ hereinbelow) of the camu camu seed extract was $IC_{50}$=0.06 mg/g in terms of the evaporation residue, indicating higher DPPH radical scavenging activity compared to $IC_{50}$=0.13 mg/g of the known antioxidative component α-tocopherol.

Referential Example 2

1 kg of camu camu seeds were crushed, mixed with 4 kg of water, and stirred at room temperature longer than overnight for extraction. After the stirring extraction, the mixture was centrifuged to separate the supernatant from the coarse residue, the residue was removed, and only the supernatant was collected. For further clarification, the supernatant was subjected to multi-stage filtration to remove fine residues. Through this operation, about 4 kg of a clear, water-soluble camu camu seed extract (1% solid) was obtained, and referred to as extract (C).

Figure 2:
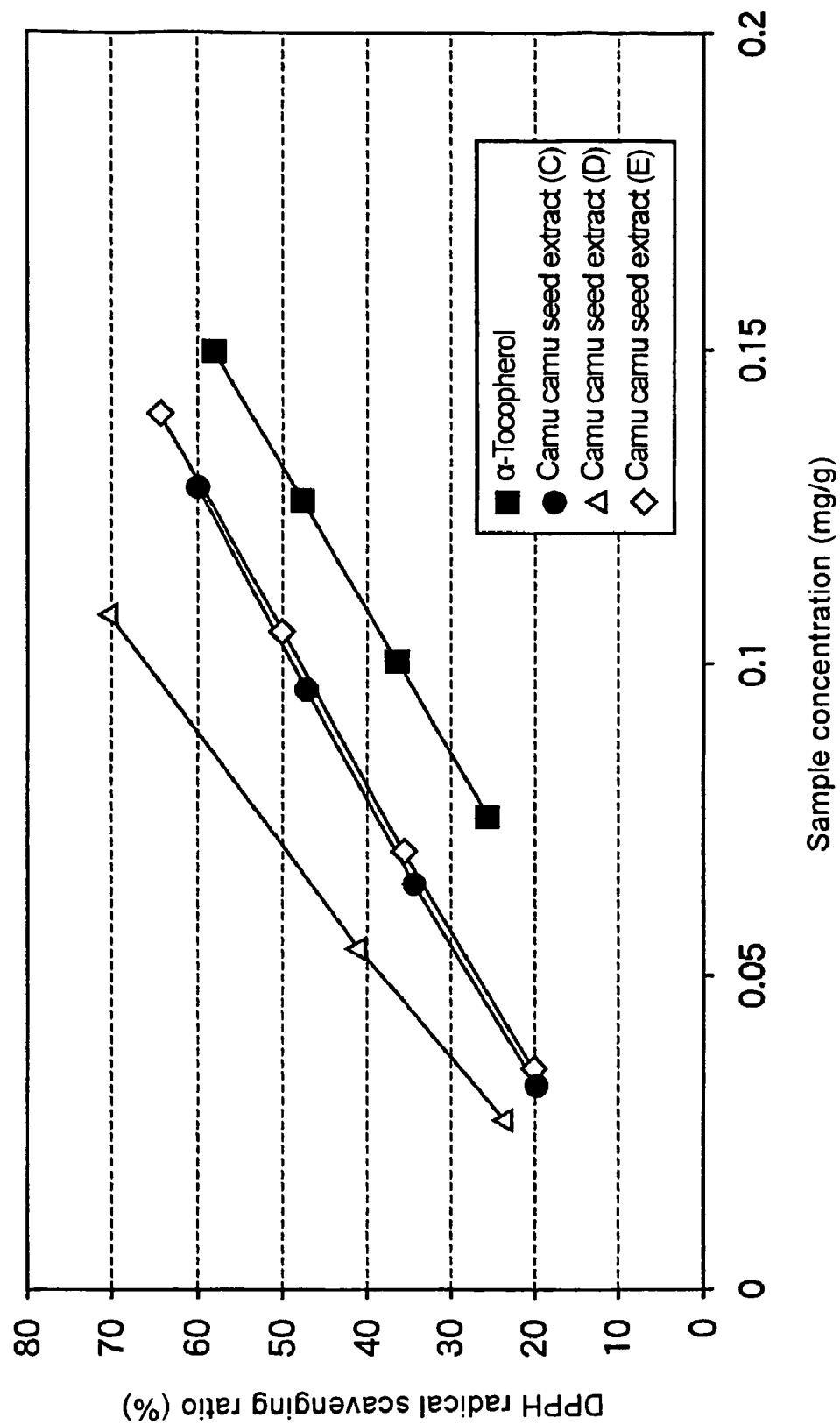
FIG. 2 is a graph showing the results of the test for measuring DPPH radical scavenging activity conducted in Referential Examples 2 to 4.

The obtained extract (C) was tested for the DPPH radical scavenging activity in the same way as in Referential Example 1. The same procedure was also performed with α-tocopherol, which is a known antioxidative component, for measuring the DPPH radical scavenging activity. The results are shown in FIG. 2. From FIG. 2, it is understood that the $IC_{50}$ of extract (C) was 0.10 mg/g, whereas the $IC_{50}$ of α-tocopherol was 0.13 mg/g.

Referential Example 3

1 kg of camu camu seeds were crushed, mixed with a mixed solvent of 1.17 kg of water and 0.5 kg of 1,3-butyleneglycol, and stirred at room temperature longer than overnight for extraction. After the stirring extraction, the mixture was centrifuged to separate the supernatant from the coarse residue, the residue was removed, and only the supernatant was collected. For further clarification, the supernatant was subjected to multi-stage filtration to remove fine residues. Through this operation, about 1.3 kg of 30% 1,3-butylene glycol extract of camu camu seeds (3% solid) was obtained, which was clear. This extract is referred to as extract (D).

The obtained extract (D) was tested for the DPPH radical scavenging activity in the same way as in Referential Example 1. The results are shown in FIG. 2. From FIG. 2, it is understood that the $IC_{50}$ of extract (D) was 0.07 mg/g.

Referential Example 4

200 g of camu camu seeds were crushed, mixed with 2 kg of ethanol, and stirred at room temperature longer than overnight for extraction. After the stirring extraction, the mixture was coasely filtered to remove the residue, and only the supernatant was collected. The supernatant was vacuum distilled to remove ethanol. The resulting dry product was dissolved in 500 g of water, and subjected to multi-stage filtration for clarification. Through this operation, about 500 g of ethanol extract of camu camu seeds (2.5% solid) was obtained, which was water-soluble and clear. This extract was referred to as extract (E).

The extract (E) was tested for the DPPH radical scavenging activity in the same way as in Referential Example 1. The results are shown in FIG. 2. From FIG. 2, it is understood that the $IC_{50}$ of extract (E) was 0.10 mg/g.

Referential Example 5

Extract (D) prepared in Referential Example 3 was tested for the linoleic acid autooxidation inhibitory effect in accordance with the following method.

<Test on Linoleic Acid Autooxidation Inhibitory Effect>

2 ml of ethanol containing 2.5% (w/v) linoleic acid and 4 ml of a 0.05 M phosphate buffer (pH 7.0) were mixed to prepare a reaction liquid. Then extract (D) was diluted with 2 ml of 99.5% ethanol and 2 ml of distilled water so that the resulting solution had an arbitrary amount of extract (D). The obtained dilution was added to the reaction liquid to make the total volume to 10 ml, mixed, and placed in a brown threaded bottle to prepare a sample.

A negative control was prepared by adding, to the reaction liquid, only 2 ml of 99.5% ethanol and 2 ml of distilled water, without adding anything else. Positive controls were prepared in the same way as for extract (D) at the same concentration, except that extract (D) was replaced with α-tocopherol or BHA. Further, in order to confirm that the antioxidative activity of extract (D) was not ascribable solely to gallic acid contained in the camu camu seed extract, a sample was prepared using gallic acid in the same way as for extract (D) and the concentration was adjusted as follows.

The concentration of gallic acid was adjusted to the maximum amount that is expected to be contained in extract (D). That is, the polyphenol content of extract (D) was measured by the Folin-Denis method, and found to be about 20%. Based on the fact that gallic acid is a polyphenol, even if all the polyphenols in extract (D) were assumed to be gallic acid, the content of gallic acid in extract (D) is at most about 20%, and possibility of a higher gallic acid content is believed to be infinitely low. Accordingly, the content of gallic acid in extract (D) was assumed to be 20%.

The samples prepared above were stored in darkness at 40° C. as main samples, and in darkness at 4° C. as blanks, and the measurements were made at intervals for 7 days.

Figure 3:
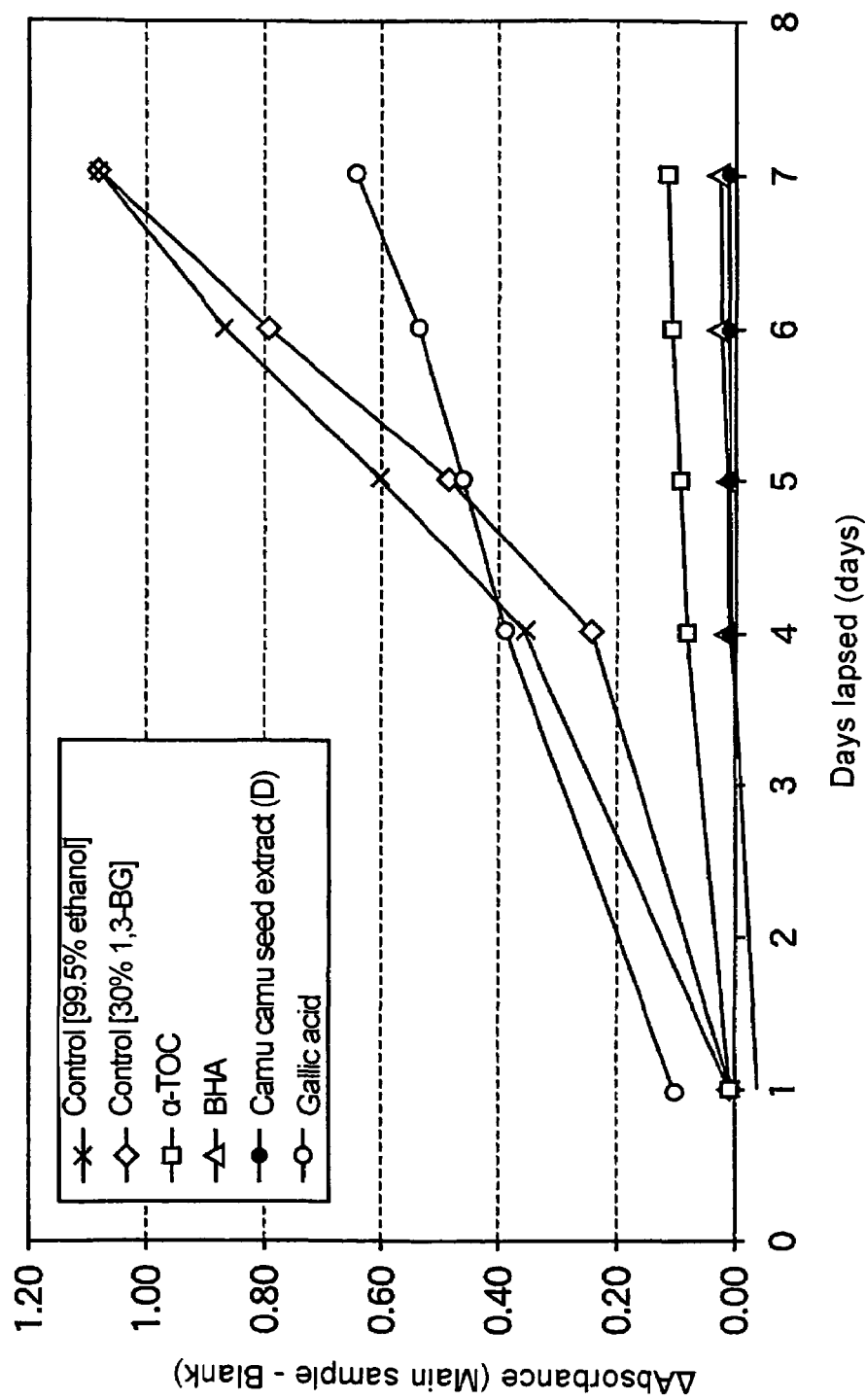
FIG. 3 is a graph showing the results of the test for measuring linoleic acid autooxidation inhibitory effect conducted in Referential Example 5.

The measurement was carried out by mixing 0.1 ml of a sample, 9.7 ml of 75% ethanol, and 0.1 ml of 30% ammonium rhodanide, adding 0.1 ml of $2\times10^{-2}$ M ferrous chloride (3.5% hydrochloric acid solution) thereto, and exactly 3 minutes later, measuring the absorbance at 500 nm. From the measured values, the difference in absorbance and the rate of autooxidation on day 7 were obtained. The same measurement was made with the blanks, and Δ Absorbance=(Absorbance of Main Sample)−(Absorbance of Blank) was taken. The results are shown in FIG. 3.

The absorbance increases with oxidation of the sample, and after reaching the maximum, decreases with consumption of the sample to be oxidized. Thus earlier occurrence of the peak absorbance represents weaker antioxidative activity.

Further, the antioxidative activities of the samples were compared in terms of the degree of oxidation. The degree of oxidation was calculated according to the following formula, with the oxidation of the control (Δ absorbance) on day 7 of the test being 100%. The results are shown in FIG. 4.

Degree of Linoleic Acid Autooxidation (%)=([Δ Absorbance of Sample]/[Δ Absorbance of Control])×100

Figure 4:
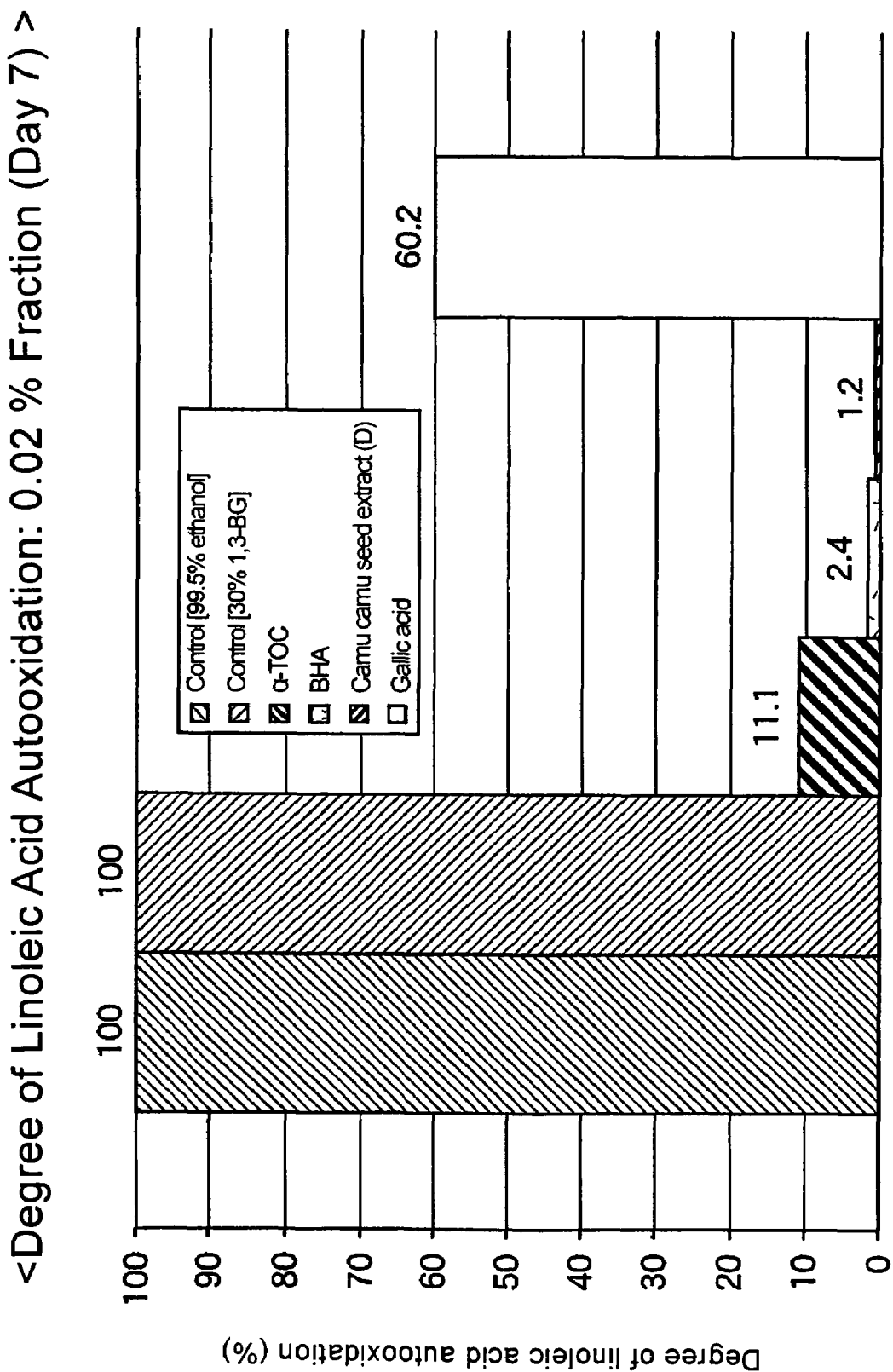
FIG. 4 is a graph showing the degree of oxidation on day 7 of each sample measured in the test on linoleic acid autooxidation inhibitory effect conducted in Referential Example 5.

From FIG. 4, it is understood that a higher value of the degree of oxidation represents lower antioxidative activity. Thus extract (D) may be concluded to have an extremely high antioxidative activity.

Example 1

Extract (D) prepared in Referential Example 3 was tested for whitening effect at cellular level, using murine B16 melanoma cells. By the use of animal cells, this test allows confirmation of the inhibitory effect on melanin formation and the effect on cell proliferation in an environment similar to that within the living body.

Petri dishes were seeded with $1\times10^5$ cells/dish of murine B16 melanoma cells, and cultured at 37° C. in 5% $CO_2$ for 2 days. After the culture solution was removed, 10 ml/dish of a test medium (blank medium (10% FBS/DME); medium adjusted with kojic acid as a control, which is a known whitening component; or medium adjusted with camu camu seed extract (D)) was added to each petri dish, and cultured at 37° C. in 5% $CO_2$ for 3 days. After the culture solution was removed, the cells were dissociated with a trypsin solution, centrifuged, suspended in PBS, and centrifuged again. The supernatant was removed, and the remaining cell pellet was mixed with a sodium hydroxide solution. The mixture was heat-treated to dissolve the melanin pigment, and fibrous materials derived from the cells were filtered out. The resulting solution was measured for the dissolved melanin pigment by means of an absorptiometer, and for a protein content by means of a DC-Protein Assay KIT manufactured by BIO-RAD.

The inhibitory effect of each sample on melanin formation was calculated by the following formula, taking the inhibitory effect of the blank medium on melanin formation as 0% as a control. The results are shown in FIG. 5.

Ratio of Inhibition of Melanin Formation (%)=100−
([Average Melanin Amount per 1 mg of Total Protein of Sample]/[Average Melanin Amount per 1 mg of Total Protein of Control])×100

In FIG. 5, a higher value of the ratio of inhibition of melanin formation represents higher whitening activity.

Thus, it is understood that camu camu seed extract (D) has extremely high whitening activity.

Further, since the total protein amount is in proportion to the cell count, the total protein amount of each test medium was measured, and its effect on cell proliferation was tested. The results are shown in FIG. 6.

From FIG. 6, no problem was observed in the effect of each sample on cell proliferation. Further microscopic observation revealed no problem.

Example 2

Safety tests were conducted on camu camu seed extract (D) prepared in Referential Example 3 in accordance with The Ordinance No. 21 regarding Good Laboratory Practice dated Mar. 26, 1997, by Ministry of Health and Welfare, Japan. The results are shown in Table 1.

Single Oral Dose Toxicity Study in Rats

Two groups (control and administered groups) of rats each consisting of five males and five females were used. The administered group was given 2 g/kg body weight of the extract.

Skin Primary Irritation Test in Guinea Pigs

Three guinea pigs were exposed to the extract by occlusive patch on healthy skin for 24 hours. At 24, 48, and 72 hours after the administration, the skin conditions were observed and evaluated.

14-Day Skin Accumulative Irritation Test in Guinea Pigs

Three guinea pigs were exposed to the extract by application on healthy skin once a day in an open system for 14 consecutive days. During the test period, the skin conditions were observed and evaluated every day at 24 hours before and after the application.

Skin Sensitization Study in Guinea Pigs

Three groups of guinea pigs (control, applied, and DNCB groups) consisting of 5 animals each were tested in accordance with the Adjuvant and Patch Test method, and the skin conditions were observed and evaluated at 24 and 48 hours after the application.

Skin Phototoxicity Study in Guinea Pigs

Ten guinea pigs were tested on the back skin in accordance with the method of Fujiou Morikawa et al., and the skin conditions were observed and evaluated at 24, 48, and 72 hours after the UV irradiation.

Skin Photosensitization Study in Guinea Pigs

Three groups of guinea pigs (control, administered, and TCSA groups) consisting of 5 animals each, were tested in accordance with the Adjuvant and Strip method, and the skin conditions were observed and evaluated at 24 and 48 hours after the UV irradiation.

Eye Mucosal Irritation Test in Rabbits

Two groups of rabbits (non-eyewashed and eyewashed groups) consisting of three animals each were used. After administration of the eye drops, the non-eyewashed group was not treated, while the eyewashed group was subjected to eye flush with tipid saline for about 1 minute. At 1, 24, 48, and 72 hours after that, the conditions of the cornea, iris, and conjunctiva were observed, and evaluated in accordance with the AFNOR standard.

Reverse Mutation Test in Bacteria

Measurements were made in accordance with the preincubation assay with or without S9mix added. Bacterial strains used: *Salmonella typhimurium* TA100, TA98, TA1535, TA1537

Bacterial strains used: *Escherichia coli* WP2uvrA

Chromosomal Aberration Assay in Cultured Mammalian Cells

Three groups (negative control, tested substance, and positive control groups) of cultured mammalian cells (CHL/IU cells) were used, and evaluated by the short-term treatment method (6 hours of treatment, with or without S9mix added) and the continuous treatment method (24 and 48 hours of treatment).

TABLE 1

| List of Safety Tests | Results |
|---|---|
| 1) Single oral dose toxicity study in rats | not toxic |
| 2) Skin primary irritation test in guinea pigs | not irritative |
| 3) 14-Day skin accumulative irritation test in guinea pigs | not irritative |
| 4) Skin sensitization study in guinea pigs | not sensitizable |
| 5) Skin phototoxicity study in guinea pigs | not phototoxic |
| 6) Skin photosensitization study in guinea pigs | not photosensitizable |
| 7) Eye mucosal irritation test in rabbits | not eye irritative |
| 8) Reverse mutation test in Bacteria | not mutagenic |
| 9) Chromosomal aberration assay in cultured mammalian cells | no aberration |

Referential Example 6

The collagenase inhibitory effects of extract (C) prepared in Referential Example 2, extract (D) prepared in Referential Example 3, and extract (E) prepared in Referential Example 4 were measured in accordance with the following process, using gallic acid monohydrate for comparison.

<Test on Collagenase Inhibitory Activity>

[Preparation of Reagent]

Substrate solution: 0.39 mg of Pz-peptide (manufactured by BACHEM AG) was dissolved in 1 ml of a 0.1 M Tris-HCl buffer (pH 7.1, containing 20 mM calcium chloride) for use (equivalent to 0.5 mM).

Enzyme solution: 5 mg of collagenase (TYPE IV, manufactured by SIGMA) was dissolved in 1 ml of distilled water, divided into aliquots of 100 µl each, and stored at −20° C. Each aliquot was diluted 50 times with distilled water upon use for reaction.

Each of extracts (C), (D), and (E), all of which were in solution forms, was diluted with its extractant (distilled water, 30 wt % 1,3-butylene glycol), so that the content of the extract as dry solid was 100 µg/ml, to prepare sample solutions. 50 µl of each sample was mixed with 50 µl of the enzyme solution and 400 µl of the substrate solution, and incubated at 37° C. for 30 minutes. Then the reaction was terminated with 1 ml of a 25 mM citric acid solution, and the resulting solution was extracted with 5 ml of ethyl acetate. After centrifuging (3000 rpm, 10 minutes), the ethyl acetate layer was collected, and the absorbance at 320 nm was measured, using ethyl acetate as a standard.

As a control against each sample, its extractant was used. A blank for each solution was prepared by the same operation, with the enzyme solution being replaced with distilled water.

Here, in order to confirm that the collagenase inhibitory activities of the camu camu seed extracts were not ascribable solely to the gallic acid contained in the camu camu seed extracts, another sample was prepared with gallic acid monoanhydrate and adjusted to 100 µg/ml with distilled water, which is the same concentration as the extracts.

From the obtained values, the degree of inhibition of collagenase activity was calculated in accordance with the following formula. The results are shown in FIG. 7.

Degree of Inhibition of Collagenase Activity (%)=
(1−[Absorbance of Sample−Absorbance of Blank for Sample]/[Absorbance of Control−Absorbance of Blank for Control])×100

Referential Example 7

The hyaluronidase inhibitory effect of extract (D) prepared in Referential Example 3 was measured in accordance with the following method of Yumie Maeda et al (Shokueishi, Vol. 31, p 233–237, 1990), which is based on the Morgan-Elson method, using gallic acid monohydrate for comparison.

<Test on Hyaluronidase Inhibitory Effect>

[Preparation of Reagents]

Enzyme solution: Bovine testis hyaluronidase (manufactured by WAKO PURE CHEMICAL INDUSTRIES, LTD.) was dissolved in a 0.1 M acetate buffer (pH 4.0) to have a final enzymatic activity of 400 Units/ml.

Enzyme activator solution: Compound 48/80 (manufactured by SIGMA) was dissolved in a 0.1 M acetate buffer (pH 4.0) to have a final concentration of 0.1 mg/ml.

Substrate solution: Potassium hyaluronate (manufactured by WAKO PURE CHEMICAL INDUSTRIES LTD.) was dissolved in a 0.1 M acetate buffer (pH 4.0) to have a final concentration of 0.4 mg/ml.

Boric acid solution: 50 ml of water was added to 4.95 g of boric acid, the pH was adjusted to 9.1 with a 1N sodium hydroxide solution, and the volume was adjusted to 100 ml with distilled water.

p-Dimethyl-aminobenzaldehyde (p-DAB) reagent: 10 g of p-DAB (manufactured by WAKO PURE CHEMICAL INDUSTRIES LTD.) was dissolved in a mixture of 12.5 ml of 10 N hydrochloric acid and 87.5 ml of acetic acid, and refrigerated. The solution was diluted ten times with acetic acid immediately before use.

Extract (D) prepared in Referential Example 3, which was in a solution form, was diluted with its extractant, a 30 wt % aqueous solution of 1,3-butylene glycol, so that the content of the camu camu seed extract as dry solid was 1 mg/ml, to prepare a sample of maximum concentration. On the other hand, the same solution was further diluted with the extractant to adjust the concentration, to prepare samples. 0.1 ml of the enzyme solution was added to 0.2 ml of each sample, and warmed at 37° C. for 20 minutes. Then 0.2 ml of the enzyme activator solution was added, and warmed at 37° C. for 20 minutes. 0.5 ml of the substrate solution was added, and reacted at 37° C. for 40 minutes. Then the reaction was stopped by adding 0.2 ml of a 0.4 N aqueous solution of sodium hydroxide and ice-cooling. 0.2 ml of the boric acid solution was added, and heated in a hot block bath (TOYO SEISAKUSHO, Model TPB-32) for 5 minutes, and the nice-cooled. 6 ml of p-DAB reagent was added, and warmed at 37° C. for 20 minutes to develop coloration. The absorbance at 585 nm was measured, using distilled water as a standard.

In a control, the sample was replaced with its extractant, and in corresponding blanks for the sample and the control, the enzyme solution was replaced with a 0.1 M acetate buffer (pH 4.0), and treated in the same way.

Here, in order to confirm that the hyaluronidase inhibitory effect of extract (D) was not ascribable solely to the gallic acid contained in the camu camu seed extract, another sample was prepared with gallic acid monoanhydrate in the same way as for extract (D), and the concentration was adjusted. The concentration of the gallic acid monoanhydrate was assumed as 20% of the dry solid of the camu camu seed extract as in Example 5.

From the obtained values, the degree of inhibition of hyaluronidase activity was calculated in accordance with the following formula. The results are show in FIG. 8.

Degree of Inhibition of Hyaluronidase Activity (%)=
(1−[Absorbance of Sample−Absorbance of
Blank for Sample]/[Absorbance of Control−
Absorbance of Blank for Control])×100

From FIG. 8, it is understood that extract (D) has a concentration-dependent hyaluronidase inhibitory activity.

Prescription Example 1

0.20 parts by weight of dipotassium glycyrrhizinate, 0.10 parts by weight of citric acid, 0.30 parts by weight of sodium citrate, 5.00 parts by weight of extract (D) prepared in Referential Example 3, and 5.00 parts by weight of 1,3-butylene glycol were mixed, and purified water was added to increase the total amount to 80.0 parts by weight. The mixture was dissolved under stirring at 50° C. to prepare an extract (D)-containing aqueous solution.

0.90 parts by weight of tetraoleic acid-POE (60) sorbitol, 0.10 parts by weight of sorbitan monooleate, a suitable amount of preservatives, and 10.00 parts by weight of ethanol were mixed, and dissolved under stirring at 50° C. Then the obtained solution was added in small portions to the previously-prepared extract (D)-containing aqueous solution, and mixed under stirring at 50° C. until the mixture became homogeneous. The temperature of the solution was lowered under stirring from 50° C. to 30° C., where the stirring was stopped. Suitable amount of flavoring agents and purified water were added to increase the total amount to 100.00 parts by weight. Then the mixture was stirred again into a homogeneous mixture to prepare a skin lotion.

Prescription Example 2

10.00 parts by weight of squalene and a suitable amount of preservatives were mixed, purified water was added to increase the total amount to 70.00 parts by weight, and the resulting mixture was heated to 80° C. to prepare solution (1). On the other hand, 0.10 parts by weight of carboxyvinyl polymer and 0.20 parts by weight of xanthan gum were dissolved in a suitable amount of purified water under stirring at room temperature to prepare solution (2). 0.10 parts by weight of triethanolamine and 5.00 parts by weight of 1,3-butylene glycol were dissolved in a suitable amount of purified water under stirring at room temperature to prepare solution (3). 2.00 parts by weight of sodium hyaluronate and 5.00 parts by weight of extract (D) prepared in Referential Example 3 were dissolved in a suitable amount of purified water under stirring at room temperature to prepare solution (4).

Next, solution (1) was added in small portions into a suitable amount of purified water, and mixed under stirring at 80° C. Solution (2), and then solution (3) were successively added under stirring. When mixed homogeneously, the mixture was cooled to 50° C. under stirring, where solution (4) was added, and purified water was added to increase the total amount to 100 parts by weight. The resulting solution was stirred again until the temperature was lowered to 30° C., where the stirring was stopped, to obtain a homogeneous emulsion.

Prescription Example 3

2.00 parts by weight of POE (20)sorbitan monostearate, 0.50 parts by weight of POE sorbitan tetraoleate, 0.50 parts by weight of glyceryl monostearate, 7.00 parts by weight of stearic acid, 3.00 parts by weight of cetyl alcohol, 3.00 parts by weight of cetyl palmitate, 7.00 parts by weight of jojoba oil, 3.00 parts by weight of paraffin, and a suitable amount of preservatives were mixed, and dissolved under stirring at 80° C. to prepare solution (1). On the other hand, 5.00 parts by weight of extract (D) prepared in Referential Example 3,7.00 parts by weight of 1,3-butylene glycol, and 62 parts by weight of purified water were mixed, and dissolved under stirring at 80° C. to prepare solution (2).

Then, solution (1) was added in small portions into solution (2), emulsified, cooled under stirring to 40° C., where the stirring was stopped, to prepare a homogeneous cream.

Prescription Example 4

54.00 parts by weight of granulated sugar was dissolved in a suitable amount of purified water, mixed with 41.70 parts by weight of starch syrup, heated, and boiled down. Then 1.00 parts by weight of citric acid and 0.30 parts by weight of flavoring agents were added in small portions under homogeneous stirring, cooled down to 90° C. under stirring, mixed with 3.00 parts by weight of extract (C) prepared in Referential Example 2, and stirred. The resulting homogeneous mixture was molded by conventional means to obtain candies.

Prescription Example 5

32.00 parts by weight of sugar was added in small portions to 65.00 parts by weight strawberry fruit, and heated under stirring to boil down. When the sugar concentration exceeded 65%, the heating was stopped, and 2.50 parts by weight of extract (C) prepared in Referential Example 2,0.15 parts by weight of citric acid, and a suitable amount of flavoring agent were added and mixed homogeneously. The resulting concentrate was packed in a bottle while hot, sterilized, and rapidly cooled to prepare jam.

Example 3

0.1 parts by weight of sodium citrate, 1.0 parts by weight of sodium pyrrolidone carboxylate, and 3.5 parts by weight of 1,3-butylene glycol were mixed, and purified water was added to increase the total amount to 50.0 parts by weight. The mixture was stirred at 50° C. to dissolve, to thereby prepare solution (1). On the other hand, 0.6 parts by weight of POE (30) POP (6) decyltetradecyl ether, 10.0 parts by weight of ethanol, and 0.1 parts by weight of methylparaben were mixed, and dissolved under stirring at 50° C. to prepare solution (2).

Solution (1) was added in small portions into solution (2) under stirring at 50° C., and further stirred to cool to 30° C., where 5.0 parts by weight of camu camu seed extract (D)

prepared in Referential Example 3 was added and mixed. Then purified water was added to increase the total amount to 100 parts by weight, and stirred to mix homogeneously to prepare a 5 wt % blended skin lotion.

Similarly, a 1 wt % blended skin lotion was prepared in the same way as above except that 4.7 parts by weight of 1,3-butylene glycol and 1.0 parts by weight of camu camu seed extract (D) were used.

Further, a blank skin lotion was also prepared in the same way as above except that 5.0 parts by weight of 1,3-butylene glycol was used and no camu camu seed extract (D) was added.

The resulting skin lotion preparations were tested for antioxidative activity of the skin lotions containing camu camu seed extract by means of the test for measuring DPPH radical scavenging activity.

<Test for Measuring DPPH Radical Scavenging Activity>

(Test Procedure)

The antioxidative activities of the skin lotion preparations containing 1 wt % and 5 wt % camu camu seed extract (D), respectively, prepared above were measured in accordance with the method in Referential Example 1, using the blank skin lotion as a control. From the measured values, the DPPH radical scavenging ratios were calculated.

(Test Result)

The DPPH radical scavenging ratios of the skin lotion preparations containing 5 wt % and 1 wt % camu camu seed extract (D) were 87.2% and 26.8%, respectively. From these values, it is understood that a skin lotion preparation having a higher content of camu camu seed extract exhibits higher antioxidative activity.

What is claimed is:

1. A whitening agent comprising camu camu seed extract as an active component, wherein the whitening agent does not comprise camu camu pulp extract.

2. The whitening agent of claim 1, wherein said camu camu seed extract contains at least one of gallic acid and salts thereof.

3. A skin preparation for external use comprising the whitening agent of claim 1.

4. A cosmetic comprising the whitening agent of claim 1.

5. A whitening agent comprising camu camu seed extract as an active component, wherein the vitamin C content of the camu camu seed extract is 1 mg/100 g or less.

6. The whitening agent of claim 5, wherein said camu camu seed extract contains at least one of gallic acid and salts thereof.

7. A skin preparation for external use comprising the whitening agent of claim 5.

8. A cosmetic comprising the whitening agent of claim 5.

* * * * *

Disclaimer

7,192,617 B2 - Kenichi Nagamine; Miki Hayashi, both of Tokyo (JP); Kaori Yamasaki, Nagasaki, (JP). WHITENING AGENT, SKIN PREPARATION FOR EXTERNAL USE AND COSMETIC. Patent dated March 20, 2007. Disclaimer filed August 5, 2021, by the assignee, Nichirei Biosciences Inc.

I hereby disclaim the following complete claim 1-8 of said patent.

*(Official Gazette, July 26, 2022)*